United States Patent [19]

Paghdiwala

[11] Patent Number: 5,401,171
[45] Date of Patent: Mar. 28, 1995

[54] DENTAL LASER DEVICE AND METHOD

[76] Inventor: Abid F. Paghdiwala, 4739 Fredonia Pl., Bensalem, Pa. 19020

[21] Appl. No.: 915,293

[22] Filed: Jul. 20, 1992

[51] Int. Cl.⁶ .................... A61C 5/00; A61C 1/00; A61C 3/00
[52] U.S. Cl. ..................... 433/215; 433/29; 606/3; 606/13
[58] Field of Search ............ 433/29, 315, 229; 606/13, 14, 17, 18, 3

[56] References Cited

U.S. PATENT DOCUMENTS

| | | | |
|---|---|---|---|
| 4,539,987 | 9/1985 | Nath et al. | 606/13 X |
| 4,849,859 | 7/1989 | Nagasawa | 606/17 X |
| 4,856,512 | 8/1989 | Lombardo et al. | 606/13 |
| 4,913,132 | 4/1990 | Gabriel | 606/14 X |
| 4,940,411 | 7/1990 | Vassiliadis et al. | 433/29 X |
| 5,020,995 | 6/1991 | Levy | 433/215 |
| 5,055,048 | 10/1991 | Vassiliadis et al. | 433/215 |
| 5,074,861 | 12/1991 | Schneider et al. | 606/17 |
| 5,118,293 | 6/1992 | Lery | 433/215 |
| 5,123,845 | 6/1992 | Vassiliadis et al. | 433/215 |
| 5,151,029 | 9/1992 | Levy | 433/29 |
| 5,151,031 | 9/1992 | Levy | 433/215 X |
| 5,151,096 | 9/1992 | Khoury | 606/17 X |
| 5,169,318 | 12/1992 | Levy | 433/215 X |
| 5,192,279 | 3/1993 | Samuels et al. | 606/17 |
| 5,199,870 | 4/1993 | Steiner et al. | 433/215 X |

OTHER PUBLICATIONS

ICALEO Proceedings, vol. 64 Oct. 30–Nov. 4, 1988, "Application of the Erbium: YAG Laser on Hard Dental Tissues, Abid F. Paghdiwala".
"Effect of Erbium: YAG laser Radiation on Hard Dental Tissues" A. F. Paghdiwala et al., 1987.
"Does The Laser Work On Hard Dental Tissue?" A. F. Paghdiwala, D. M. D. JAMDA Jan. 1991 pp. 79–80.
"Root Resection of Endodontically Treated Teeth by Erbium: YAG Laser Radiation" A. F. Paghdiwala, D. M. D. Journal of Endodontics, vol. 19, No. 2, Feb. 1993, pp. 91–93.

Primary Examiner—Gene Mancene
Assistant Examiner—Nicholas D. Lucchesi
Attorney, Agent, or Firm—Reed Smith Shaw & McClay

[57] ABSTRACT

A dental laser apparatus and method are disclosed, wherein the laser energy is generated within a handheld handpiece. When the laser is activated, pulsed laser energy generated within the handpiece is focused by a lens, also situated within the handpiece, onto the tissues in the mouth. The laser is preferably an Erbium:YAG laser, which can cut soft tissue, hard tooth tissue such as enamel and dentin, and bone, without causing structural or pulpal damage to the teeth or other tissues in the mouth.

3 Claims, 1 Drawing Sheet

DENTAL LASER DEVICE AND METHOD

BACKGROUND OF THE INVENTION

1. Field of the Invention

The present invention relates in general to medical lasers and in particular to a dental laser method and apparatus for performing surgical procedures involving the soft tissues, teeth and bone in the oral cavity.

2. Description of the Prior Art

The procedures dentists perform in the oral cavity usually involve either correcting diseases or defects of soft tissues, for which scalpels and similar surgical instruments are used, or for correcting diseases of the hard tissues, such as enamel and dentin of the teeth, for which mechanical drills are used. In addition, for some procedures, such as certain periodontal surgical procedures, and for removal of impacted wisdom teeth, removal of bone is also involved, usually by mechanical drills, chisels and the like. All these procedures usually cause discomfort to the patient.

In recent years, dental lasers have been used by dentists. Two kinds of lasers, the Neodymium:Yttrium-Aluminum-Garnet (Nd:YAG) and the Carbondioxide (CO2) lasers have been used by dentists, but only for soft tissue surgery in the mouth. Another kind of laser, the Argon laser, is used by dentists mainly for polymerization of certain kinds of materials used for filling cavities. However, studies have shown that what patients undergoing dental treatment dislike most are the grinding sensation and the whirring noise of the mechanical drills used by the dentist for drilling teeth. Many patients avoid timely dental care out of fear of the mechanical drills. Neither the Nd:YAG, CO2 or Argon lasers can be used for drilling of teeth, for reasons that will be shown below.

U.S. Pat. No. 4,521,194 to Myers et al disclosed a method for removing incipient decay from teeth and U.S. Pat. No. 4,818,230 to Myers et al disclosed a method for removing decay from teeth. Both the above-mentioned patents disclosed the use of a Nd:YAG laser for removing the decay by exposing the decayed dentin of the tooth to the laser. However, the currently acceptable method in dentistry of treating tooth decay involves removal of not just the decayed dentin of the teeth as is taught by the above-mentioned patents but rather also involves removal of the surrounding sound, healthy, intact enamel at the margins of the decayed area. This is intended to ensure that when the cavity is filled, the margins of the filling will be so shaped and situated as to ensure success of the completed filling. Therefore, for a laser to be useful for drilling teeth, that laser would also have to be able to cut sound enamel and dentin and not just remove decayed dentin. Neither the Nd:YAG nor the CO2 lasers have been shown in studies to cut sound, intact enamel and dentin without causing structural damage to the tooth and without heating the tooth pulp to temperatures that would cause irreversible pulp damage. Therefore, the lasers and methods disclosed in the above-mentioned patents cannot be utilized for cutting hard tooth tissue, and dentists still have to use the mechanical drill.

U.S. Pat. No. 4,940,411 to Vassiliadis et al disclosed a dental laser assembly capable of removing decayed portions of teeth, capable of desensitizing teeth and removing soft tissues. However, their invention also could not remove sound, healthy intact enamel. Therefore a dentist using their laser assembly would still have to use a conventional, mechanical drill to accomplish restoration of tooth decay.

U.S. Pat. No. 5,020,995 to Levy also disclosed that decayed tooth tissue can be cut with a Nd:YAG laser; and that if the Nd:YAG laser would be used to cut healthy tooth tissues such as healthy, intact enamel and dentin, a dark spot would first have to be formed at the portion to be cut, by applying graphite from a lead pencil onto the tooth. However, the graphite would be applied to only the most superficial layer of enamel, and once that superficial layer of enamel was cut with the laser, the graphite would have to be reapplied and when that layer was cut the dentist would have to stop the laser and reapply the graphite. Therefore, to complete the cutting process, repeated stoppage and reapplication of the graphite would be necessary and that would be awkward and inconvenient and not practical. The repeated application of graphite on a tooth in a patient's mouth would also pose a health hazard to the patient; in addition, plume resulting from the interaction of the laser with the graphite on a patient's tooth may pose an additional risk to dentist and patient.

Recent studies have shown that laser energy radiating at certain other wavelengths is considerably better suited for cutting sound dental enamel and dentin. In particular, the pulsed Erbium:Yttrium-Aluminum-Garnet (Erbium:YAG) laser, having a wavelength of 2.94 microns, has been shown to not only remove decay but also cut sound enamel and dentin without causing structural damage to the tooth and without causing temperature rise of the tooth pulp beyond the 5 degrees C. threshold for irreversible pulp damage. Therefore, for treating decayed teeth, the Erbium:YAG laser can be used not only to remove the decayed part of the tooth but also to cut the healthy enamel and dentin at the margins of the decayed portion for acceptable cavity restoration. In addition, the Erbium:YAG laser can also be used to cut the intact enamel and dentin overlying the tooth pulp chamber so as to get access to the root canal to initiate root canal therapy. None of the lasers of the prior art teaches cutting enamel and dentin with a laser to get access to the pulp chamber to initiate root canal therapy. The Erbium:YAG laser can also be used to section the roots of teeth in root resection surgical procedures.

The Erbium:YAG laser has also been shown to be very effective for soft tissue surgical procedures due to its very high absorption in the cellular fluids of the soft tissues as compared to both the CO2 laser and the Nd:YAG laser. The 2.94 micron Erbium:YAG laser output coincides with the major water absorption band which peaks around 3.0 microns. In fact, the absorption of the Erbium:YAG laser in water is ten times greater than the absorption of the CO2 laser in water and almost 20,000 times greater than the absorption of the Nd:YAG laser in water. When laser energy is absorbed by the water in the cells in the body, laser light produces an intense thermal reaction which leads to vaporization of the cellular contents and eventual disruption of the cells. If a laser is very highly absorbed by the cellular fluids, its cutting efficiency is high, the resultant surgical incision has a narrower zone of thermal damage around it and post-operative healing is better.

The high water absorption of the Erbium:YAG laser is also believed to be responsible for the efficient cutting of enamel and dentin with the Erbium:YAG laser.

Moreover, the Er:YAG laser has also been shown in studies to be capable of cutting bones without causing necrosis of the bone cells.

Thus it would appear that the Er:YAG laser is one laser that could be used by the dentist for soft tissue, hard tissue and bone removal procedures. However, the Er:YAG laser has not found application in dental practice. This is because the Er:YAG laser has, until now, lacked an adequate delivery system to convey the laser energy from the laser head, where the laser energy is generated, to the patient's mouth. Silica optical fibers, which are so successful in conveying the laser energy in dental lasers of the prior art, such as the Nd:YAG laser, cannot conduct laser radiation beyond wavelength of approximately 2.5 microns. Therefore, silica fibers cannot convey erbium laser radiation having a wavelength of 2.94 microns. Certain other types of fibers have been tested, including zirconium fluoride fibers, but they have not been demonstrated to be successful for delivery of the Er:YAG energy without loss of energy, fracture of the fiber and/or damage to the tip of the fiber during operation. An articulated arm arrangement is typically used, connecting the laser head, where the laser energy is generated, to a hand-held tool to be used in the patient's mouth. However this articulated arm is usually bulky and awkward for surgical application in the mouth.

In U.S. Pat. No. 5,055,048, Vassiliadis et al, while disclosing a Nd:YAG dental laser, state in the specifications that an Erbium doped YAG laser has proven effective for removal of enamel. However, they too admit that at present, Erbium:YAG lasers are destructive to optical fibers of the type used their laser system, where the laser radiation is generated in a housing and is then conveyed through the optical fiber to the tissues in the patient's mouth. They, too, do not claim that their Nd:YAG laser is capable of cutting sound, healthy enamel.

What has been needed has been a method of removal of soft tissues, hard tissues and bone in the oral cavity which takes advantage of the high tissue absorption of the Er:YAG laser without the inconvenience and problems associated with an inefficient fiber or an articulated arm. Further, what has been needed has been an apparatus for application of the needed method.

SUMMARY OF THE INVENTION

The objects of the present invention are to provide an apparatus that can cut soft tissues, cut dental enamel and dentin, remove decay and cut bone; to provide an apparatus wherein laser light is generated within a hand held surgical handpiece which is constructed to be suitable for use as a hand held apparatus that can be manipulated and used by a user's hand independent of any other support.

The present invention comprises a laser assembly in which laser light is generated within a hand held surgical handpiece.

The hand held surgical handpiece comprises of a housing in which pulsed laser light having a wavelength of about 2.94 micrometers is generated. The laser is preferably an Erbium doped Yttrium-Aluminum-Garnet (Er:YAG) laser. It has been shown that laser light of 2.94 micrometers is highly absorbed by water and by the soft tissues in the oral cavity. It has also been shown that such a pulsed laser is also capable of cutting dental enamel and dentin, both decayed as well as healthy enamel and dentin. It has also been shown that the process of cutting dental enamel and dentin with the Er:YAG laser causes no structural damage to the surrounding tooth nor does it lead to heat generation and heat buildup within the tooth to the extent that would result in irreversible damage to the pulp tissue of the tooth.

One end of the housing of the hand held device is attached to an assembly that provides the power supply and coolant for the generation of the laser within the housing. Further, the hand held housing of this invention also includes a mirror assembly. The mirror is mounted at an angle of 45 degrees to the axis of the laser beam generated within the housing, and the mirror reflects the laser beam at a 90 degree angle onto a biconvex lens positioned at the distal end of the handpiece. This lens focuses the laser beam onto the soft tissue or hard tissue desired to be cut.

The advantage of the present invention is that the hand held assembly is compact, easily manipulable in the oral cavity without bulky articulated arms or inefficient fibers of the prior art. A further advantage of the present invention is that the means of generating the laser radiation, the means of controlling the direction of the laser radiation and the means of converging the laser beam and focusing the laser radiation onto the tissue are all contained within the same housing, and as such the device of the present invention will be more economical than the lasers of the prior art. The lasers of the prior art have a separate housing in which the laser radiation is generated, they have expensive assemblies to direct the laser beam from the housing into special, expensive optical fibers, they have expensive handpieces connected to these optical fibers to deliver the laser beam to the patient's mouth. Alternatively, the lasers of the prior art have separate housings to generate the laser beam, they have bulky, cumbersome, expensive articulated arms connected to the housing to direct the laser beam to expensive hand held tools that focus the laser beam onto the tissues in the patient's mouth. The articulated arms have a system of mirrors that have to be in perfect alignment to function adequately. Misalignment of the mirrors in function is a potential problem, and realignment by trained technicians can be expensive. All these disadvantages of the prior art are eliminated by the present invention.

BRIEF DESCRIPTION OF THE DRAWINGS

A better understanding of the present invention will be had upon reference to the following detailed description when read in conjunction with the accompanying drawings, wherein like reference characters refer to like parts throughout the several views, and in which.

DETAILED DESCRIPTION OF THE PREFERRED EMBODIMENT

Detailed description of the preferred embodiment of the present invention are disclosed herein.

Figure 1:
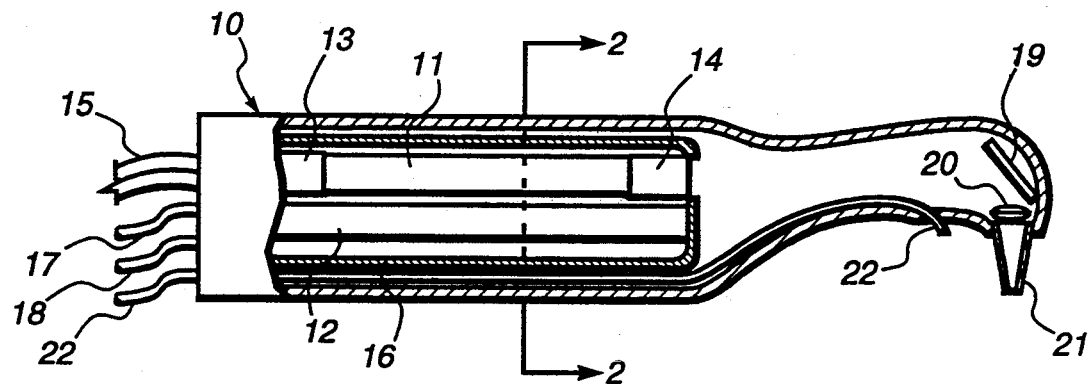
FIG. 1 is a side elevation view, in section, of the preferred embodiment of the device of the present invention.
Figure 2:
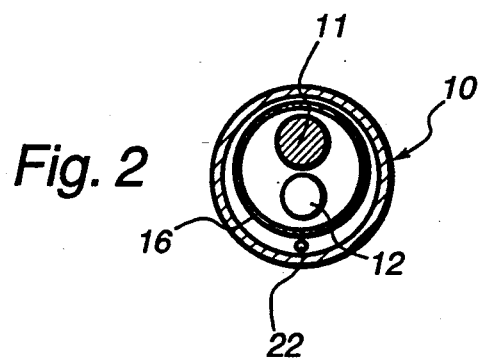
FIG. 2 is a cross section view, taken along line 2—2 of FIG. 1 of the preferred embodiment of the device of the present invention.

With reference to the Drawings, in FIG. 1, the hand held laser tool of the present invention is thereshown and comprises a housing 10. The source and the means for generation of the laser are housed within the housing 10. Upon activation of the laser, a laser beam is generated, which is transmitted longitudinally along the housing 10. The housing 10 also contains means for controlling the direction of transmission of the laser beam, comprising a mirror which reflects the laser beam at 90 degree angle and also a converging means which is mounted at distal end of the housing 10. The converging means converges the laser beam onto the surgical site in the oral cavity.

The housing 10 of the handheld laser device may be formed from any of various materials, such as plastics. Preferably, the size and shape of the housing 10 is same as a conventional dental drill. As such, the housing 10 can fit completely and comfortably within the user's hand and the distal end of the housing 10 can be easily manipulated in the patient's mouth.

In the housing 10, an Erbium:YAG (Yttrium-Aluminum-Garnet) rod 11 is located longitudinally towards the proximal end of the housing 10. A flashlamp 12 is also situated in the housing 10 and is arranged parallel to the Er:YAG rod 11. The laser rod 11 and the flashlamp 12 are supported within the housing 10 by any of the well known means.

The proximal end of the rod 11 is coated with a reflecting coating 13 which provides for 100% reflection of light back into the rod. The distal end of the rod 11 is coated with a coating 14 that is not totally reflecting but is partially transmitting so that part of the light can pass through it. An electric cable 15 from an external power supply (not shown) is connected to the housing 10 at the proximal end of the housing 10. When sufficient power is supplied to the flashlamp 12, the flashlamp 12 discharges short, high-intensity pulses of light in the housing 10. The light from the flashlamp 12 passes through the laser rod 11, thereby exciting the rod 11. As the laser rod 11 is excited, it emits photons. The photons radiating through the rod 11 strike the reflecting coating 13 at the proximal end of the laser rod 11. This reflecting coating 13 reflects the light back into the rod 11, further intensifying the level of photons emitted from the rod 11. When the photons strike the reflecting coating 14 at distal end of the rod 11, this coating 14 reflects part of the photons back into the rod 11, further amplifying the emission of photons. However, since this coating 14 at the distal end of the rod 11 is not a totally reflecting coating, it also allows part of the photons to pass through it, forming the laser beam. Mirrors situated at the ends of the laser rod may be used to replace the reflective coatings on the rod. The mirror at the proximal end of the rod can be a 100% reflecting mirror while the mirror at the distal end of the rod can be a partially reflecting, and a partially transmitting mirror.

The laser rod 11 and tile flashlamp 12 are situated within an elliptical chamber 16 situated within the housing 10. The inside lining of this elliptical chamber 16 is of a highly reflecting material such as a silver lining, so that any light from the flashlamp 12 that is scattered towards the lining of the elliptical chamber 16 is reflected back towards the laser rod 11 to increase the laser emission from the rod 11.

The process of generation of the laser, using the flashlamp 12 and the laser rod 11 generates heat. To prevent excess heat buildup during laser generation, a continuous circulation of distilled water is maintained into the elliptical chamber 16 through an inlet tube 17 and an outlet tube 18. The inlet tube 17 and outlet tube 18 are connected to a water pump (not shown). The inlet tube 17 and outlet tube 18 extend into the housing 10 at the proximal end of the housing 10 adjacent to the electric cable 15.

The laser light generated from the rod 11 is transmitted longitudinally along the housing 10 onto a mirror 19 situated within the housing 10, close to the distal end of the housing 10. This mirror 19 is preferably mounted at a 45 degree angle to the path of the laser beam and reflects the laser beam at 90 degree angle onto the converging means.

The converging means comprises a biconvex lens 20 mounted in the housing 10 so that the long axis of the lens is parallel to the long axis of the laser rod 12. The laser beam reflected from the mirror 19 is incident upon the lens 20. The lens 20 converges and focuses the laser beam which then passes through an elongate cylinder 21 onto the tissues in the patient's mouth. The elongate cylinder 21 may be formed from a variety of materials, such as plastics. The proximal end of the elongate cylinder 21 is removably mounted towards the distal end of the housing 10 and in close proximity to the lens 20. The cylinder 21 has walls of tapering cross-section and its length is sufficient to allow the focused laser beam to be focused onto the tissues in the mouth when the distal end of the cylinder 21 contacts the tissues.

The converging lens 20 can be situated between the partially reflective coating 14 and the mirror 19. The laser beam generated in the housing 10 is converged by the lens 20. The converged laser radiation is then reflected by the mirror 19 onto the desired surgical site.

In order to allow cooling of the surface being cut with the laser, especially hard tissue such as dental enamel and dentine and bone, a coolant, such as water, or air and water, is introduced to the spot where the laser beam is focused. The proximal end of a hollow tubing 22 is connected to a coolant source (not shown). This hollow tubing 22 enters the housing 10 at proximal end of the housing 10, adjacent to the electric cable 15 and the inlet tube 17 and outlet tube 18. This tubing 22 passes along the inside of the housing 10 and emerges out of the housing 10 at a point just proximal to the mounting of the elongate cylinder 21. After the tubing 22 emerges out of the housing 10, the angulation of the tubing 22 is such that when the coolant is discharged from the tubing 22, the coolant falls onto the spot where the laser beam is focused. The hollow tubing 22 can also be located in a recessed groove on the external surface of the housing 10.

The Erbium:YAG laser has a pulse duration of approximately 100 to 300 microseconds and a pulse repetition rate of between 1 and 50 Hertz. The energy per pulse can be between 0.1 millijoules and 1 Joule. The peak power will vary depending upon the pulse energy and pulse duration, and the average power will vary depending upon the energy per pulse and the pulse repetition rate. The power and energy levels selected by the user will vary depending upon the desired dental procedure. For cutting healthy enamel, for example, energy per pulse of between 30 and 300 millijoules and pulse repetition rate between 1 and 20 Hertz can be used. For resecting roots of the teeth, energy levels between 30 and 100 millijoules per pulse and pulse repetition rates between 1 and 10 Hertz are usually sufficient. For removing soft tissues, higher energy and pulse repetition rates can be used. Energy levels between 0.1 milliloule and 1 Joule per pulse and pulse repetition rates between 1 and 50 Hertz can be applied for soft tissue procedures. A coolant is supplied onto the spot where the laser beam is focused, especially when enamel, dentin and bone are being exposed to the laser.

The handheld Erbium:YAG laser can also be used for obtaining access to the pulp chamber of a tooth to initiate root canal therapy. Energy levels between 30 and 300 millijoules per pulse and pulse repetiton rates between 1 and 20 Hertz are used. Repeated exposures of the pulsed laser are made on the appropriate surface of the tooth and the enamel and dentin overlying the pulp chamber are removed and access is obtained to the pulp chamber so that an endodontic instrument can be inserted into the root canal to initiate root canal therapy.

Figure 3:
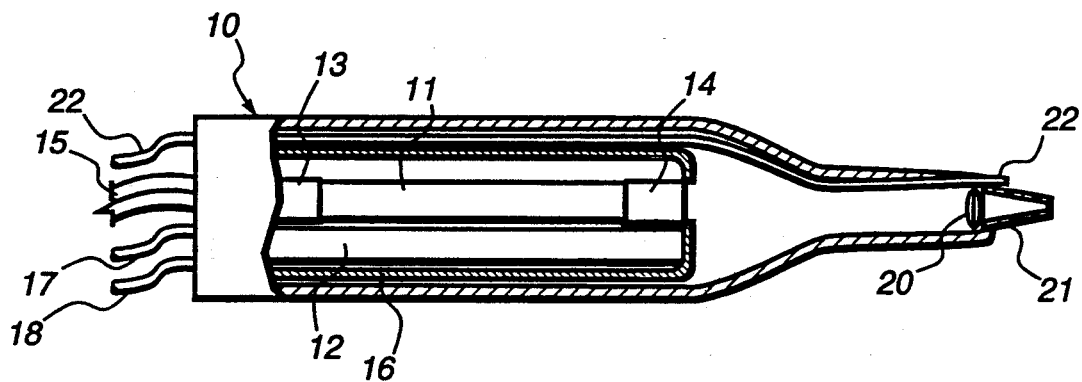
FIG. 3 is a side elevational view, in section, of another embodiment of the device of the present invention.

A second embodiment of the dental laser device of the present invention is shown in FIG. 3. In this embodiment, the laser beam generated within the hand held housing 10 is converged by the lens 20. The converged laser radiation then passes through an elongate cylinder 21, the length of the cylinder 21 being sufficient that when the tip of the cylinder touches the tissue at the desired spot, the laser beam is focused at that spot. In this second embodiment, there is no mirror to reflect the laser beam. Therefore the laser beam generated by the rod 11 remains in the same axis when it converges through the elongate cylinder 21 of the second embodiment.

A Holmium:Yttrium-Aluminum-Garnet (Ho:YAG) laser has also been shown to be capable of removing soft tissues and, to some degree, hard tissues, such as tooth tissue and bone. A Ho:YAG laser rod can be used instead of the Erbium:YAG laser rod in the hand held housing of the present-invention. Furthermore, a Nd:YAG laser rod can also be used instead of the Erbium:YAG laser rod in the hand held housing of the present invention.

From the foregoing it can be seen that the present invention provides a simple and yet highly effective handheld dental laser system for cutting hard dental tissue such as healthy and decayed dental enamel and dentin as well as cutting soft tissues. It can also be used for cutting the enamel and dentin overlying the tooth pulp chamber to gain access to the pulp chambers and root canal to initiate root canal therapy. It can also be used to resect roots of teeth requiring root resection (apicoectomy) procedure. There are many advantages to the dental laser device of the present invention.

First, the dental laser device of the present invention can cut not only decayed enamel and dentin but also sound, intact, healthy enamel and dentin. As such, a dentist attempting to restore a decayed tooth would not have to first use a mechanical drill to cut the sound enamel and dentin at the margins of the decayed lesion. The patient would be spared the fear and discomfort of the grinding and whirring of the mechanical drill.

A further advantage of the dental laser device of the present invention is that it combines the excellent performance of the Erbium laser on dental enamel and dentin, because of the strong water absorption of the Erbium laser radiation, with the ease and convenience of a hand-held device. The means for laser radiation generation and the means of directing the laser radiation on the tissue in the patient's mouth are housed within a housing constructed to be used and manipulated as a handheld device, capable of being introduced into a patient's mouth. As such this invention overcomes the difficulty of inefficient fibers or bulky articulated arms that would have to be used if the laser means was in a separate housing from the means of directing the laser radiation onto the tissues.

A still further advantage of the dental laser device of the present invention is that the elongate cylinder, which comes in contact with tissues, is removable and replaceable, ensuring sterilization and patient's protection. In addition, research studies have shown that for optimum cutting of tissues with a laser, a focused laser should be employed. In the laser device of this invention, since the laser beam is focused at the spot where the elongate cylinder 21 touches the tissues, as long as the dentist maintains contact of the end of the elongate cylinder 21 with the tissues, he will be employing a focused beam for the cutting of the tissues. Also, since the focal point of the laser beam is at the end of the cylinder 21, the dentist has a precise knowledge of the exact spot that he is cutting. Moreover, since the elongate cylinder is constructed of rigid plastic, it provides the dentist a much better tactile feel of the tissue he is contacting as compared to the lack of tactile feeling experienced by dentists using the soft, flexible silica fibers used in the lasers of the prior art.

The foregoing description of the preferred embodiment of the invention has been presented for the purpose of illustration and description. It is not intended to be exhaustive or to limit the invention to the precise form disclosed. Many changes, modifications, variations and other uses and applications to the invention are possible in light of the above teaching and will become apparent to these skilled in the art to which it pertains without deviating from the spirit of the invention. It is intended that the scope of the invention be limited not by this detailed description, but rather by the true spirit and scope of the claims appended thereto.

What is claimed is:

1. A method of performing surgical procedures on tissues in an oral cavity, said tissues including, but not limited to, oral soft tissue, bone, sound dentin, intact enamel, decayed tooth material, tooth root and tooth material overlaying the tooth pulp chamber, comprising the steps of:

positioning a hand-held device in proximity to said tissues;

generating from within said device a pulsed Er:YAG laser beam capable of cutting said soft or hard tissues which are healthy or decayed by vaporization of the cellular contents and disruption of the cells while avoiding undesirable damage to said tissues and surrounding tissues;

reflecting and controlling the direction of said laser beam in said device after said laser beam has been generated;

converging said laser beam with a converging means;

focusing said laser beam onto said tissues through an elongated removable cylinder attached to said device; and cooling said device internally.

2. A method as set forth in claim 1 wherein said laser beam has a pulse duration of approximately 100 to 300 microseconds, a pulse repetition rate of between 1 and 50 Hertz, and energy per pulse between 0.1 millijoules and 1 Joule.

3. A method as set forth in claim 2 wherein the wavelength of said laser beam is approximately 2.94 to 3.0 microns.

* * * * *